(12) United States Patent
Ishikawa et al.

(10) Patent No.: US 10,124,193 B2
(45) Date of Patent: Nov. 13, 2018

(54) X-RAY THERAPY SYSTEM AND IRRADIATION FIELD DETERMINING METHOD

(71) Applicants: HITACHI, LTD., Tokyo (JP); NATIONAL UNIVERSITY CORPORATION HOKKAIDO UNIVERSITY, Hokkaido (JP)

(72) Inventors: Masayori Ishikawa, Hokkaido (JP); Mitsuhiro Yoshida, Tokyo (JP); Takanobu Handa, Tokyo (JP); Tatsufumi Aoi, Tokyo (JP)

(73) Assignees: HITACHI, LTD., Tokyo (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 661 days.

(21) Appl. No.: 14/380,968

(22) PCT Filed: Dec. 25, 2012

(86) PCT No.: PCT/JP2012/083484
§ 371 (c)(1),
(2) Date: Aug. 26, 2014

(87) PCT Pub. No.: WO2013/128770
PCT Pub. Date: Sep. 6, 2013

(65) Prior Publication Data
US 2015/0065870 A1    Mar. 5, 2015

(30) Foreign Application Priority Data
Feb. 29, 2012 (JP) ................................. 2012-044535

(51) Int. Cl.
*A61N 5/10* (2006.01)
*A61B 6/03* (2006.01)
*A61B 6/00* (2006.01)

(52) U.S. Cl.
CPC ............ *A61N 5/1081* (2013.01); *A61B 6/032* (2013.01); *A61B 6/037* (2013.01); *A61B 6/4417* (2013.01);
(Continued)

(58) Field of Classification Search
CPC ....... A61B 6/032; A61B 6/4417; A61B 6/037; A61N 5/1081; A61N 5/1049; A61N 5/1039; A61N 2005/1091; A61N 2005/1052
See application file for complete search history.

(56) References Cited

U.S. PATENT DOCUMENTS

2006/0113482 A1  6/2006 Pelizzari et al.
2011/0084211 A1* 4/2011 Yamaya ............... A61B 6/037
                                                 250/363.03
(Continued)

FOREIGN PATENT DOCUMENTS

CN    101879071    11/2010
EP    1 860 465    11/2007
(Continued)

OTHER PUBLICATIONS

First Office Action issued Dec. 4, 2015 in Chinese Application No. 201280070714.9 (with English translation).
(Continued)

*Primary Examiner* — Peter Luong (57) ABSTRACT

An X-ray therapy system includes a gantry, a positron emission tomography (PET) detection device in the gantry, and an irradiation unit in the gantry (and configured to radiate X-rays to a patient. The PET detection device has a
(Continued)

pair of photon detection units and photon detection unit-moving devices configured to move the pair of photon detection units with respect to the gantry.

10 Claims, 9 Drawing Sheets

(52) U.S. Cl.
CPC .......... *A61N 5/1049* (2013.01); *A61N 5/1039* (2013.01); *A61N 2005/1052* (2013.01); *A61N 2005/1091* (2013.01)

(56) References Cited

U.S. PATENT DOCUMENTS

| | | | |
|---|---|---|---|
| 2011/0092814 A1 | 4/2011 | Yamaya et al. | |
| 2011/0198502 A1 | 8/2011 | Tonami | |
| 2012/0035470 A1* | 2/2012 | Kuduvalli | A61B 6/00 600/427 |
| 2012/0165651 A1* | 6/2012 | Yamaya | A61N 5/1049 600/411 |

FOREIGN PATENT DOCUMENTS

| | | |
|---|---|---|
| JP | 2000-105279 | 4/2000 |
| JP | 2005-121530 | 5/2005 |
| JP | 2008-200092 | 9/2008 |
| JP | 4311163 | 8/2009 |
| JP | 2012-5888 | 1/2012 |
| JP | 2012-5889 | 1/2012 |
| JP | 2012-10759 | 1/2012 |
| WO | 2010/013346 | 2/2010 |
| WO | 2010/141583 | 12/2010 |
| WO | 2012/021459 | 2/2012 |

OTHER PUBLICATIONS

International Search Report issued Jan. 22, 2013 in corresponding International Application No. PCT/JP2012/083484.
Translation of Written Opinion of the International Searching Authority issued Jan. 22, 2013 in corresponding International Application No. PCT/JP2012/083484.
Extended European Search Report issued Sep. 4, 2015 in corresponding European Patent Application No. 12869756.2.

* cited by examiner

3min

FIG. 10

X-RAY THERAPY SYSTEM AND IRRADIATION FIELD DETERMINING METHOD

CROSS-REFERENCE TO RELATED APPLICATION

Priority is claimed from Japanese Patent Application No. 2012-044535, filed Feb. 29, 2012, the content of which is incorporated herein by reference.

TECHNICAL FIELD

The present invention relates to an X-ray therapy system and an irradiation field determining method.

BACKGROUND ART

Conventionally, a system into which a device for performing computed tomography (CT) and a device for performing positron emission tomography (PET) are integrated is known. For example, in Japanese Unexamined Patent Application, First Publication No. 2005-121530 (hereinafter "JP 2005-121530"), a medical image diagnosis device including a CT gantry for performing X-ray examination and a PET gantry for performing PET examination is disclosed. According to the device disclosed in JP 2005-121530, it is possible to perform the X-ray CT examination and the PET examination by moving the patient from one gantry to the other gantry.

In addition, technology for performing the PET examination using a PET examination device to specify the position of a lesion portion when the therapy of the lesion portion is performed by radiating radiation to the lesion portion such as a cancer tissue is known. In this case, the irradiation of the radiation may be performed by moving a bed on which the patient lies to a radiation therapy device after the PET examination is performed.

However, when the PET examination device and the radiation therapy device are divided and separately arranged, it is necessary to move the patient from the PET examination device to the radiation therapy device. In such cases, it is difficult to radiate radiation to a position of the lesion portion obtained using the PET examination device and a position accurately corresponding to other diagnosis information.

In addition, even when the bed on which the patient lies as disclosed in JP 2005-121530 is moved, the position of the patient on the bed is likely to change with the movement of the bed and accurate position alignment is difficult.

SUMMARY OF INVENTION

Technical Problem

The present invention has been made in view of the above-described circumstances, and an objective of the invention is to provide a radiation therapy system (for example, an X-ray therapy system) and an irradiation field determining method for accurately reflecting a result of detecting a position of a lesion portion through PET examination in an irradiation position of radiation.

Solution to Problem

According to a first aspect of the present invention, an X-ray therapy system includes: a ring-shaped gantry in which a patient is arranged; a positron emission tomography (PET) detection device provided in the gantry and configured to perform PET on the patient; an irradiation unit provided in the gantry and configured to radiate X-rays to the patient; and a rotation-driving unit for causing the gantry to perform a rotational movement around a predetermined rotation center. The PET detection device includes a pair of photon detection units arranged to interpose the patient and to be opposed to each other, to detect photons emitted from the patient based on nuclear decay of a tracer nuclide administered to the patient; and a photon detection unit-moving device connected to each of the pair of photon detection units and the gantry and configured to move the pair of photon detection units with respect to the gantry. The rotation-driving unit causes the irradiation unit and the PET detection device to perform the rotational movement around the predetermined rotation center by causing the gantry to perform the rotational movement around the predetermined rotation center. The photon detection unit-moving device is configured to arrange the pair of photon detection units at positions separated from the patient by a predetermined distance when detecting photons in the PET and is configured to move the pair of photon detection units to retraction positions separated from the patient by a distance which is greater than the predetermined distance before irradiation of the X-rays starts when the X-rays are radiated from the irradiation unit to the patient.

According to a second aspect of the present invention, in the X-ray therapy system according to the first aspect, the retraction position is located outside an irradiation range of the X-rays and outside a range in which scattered rays due to the X-rays are capable of reaching the pair of photon detection units, and the predetermined distance is set within the irradiation range of the X-rays or within the range in which the scattered rays due to the X-rays are capable of reaching the pair of photon detection units.

Also, when the detection position is outside the irradiation range of the X-rays, the retraction of the pair of photon detection units is unnecessary.

According to a third aspect of the present invention, in the X-ray therapy system according to the first aspect, a pair of concave portions into which the pair of photon detection units are inserted are opened in an inner circumferential surface of the gantry, and an inside of the concave portion is the retraction position.

According to a fourth aspect of the present invention, in the X-ray therapy system according to the first aspect, the pair of photon detection units are arranged to interpose the predetermined rotation center and to be opposed to each other.

According to a fifth aspect of the present invention, in the X-ray therapy system according to the first aspect, the pair of photon detection units are arranged to interpose an isocenter and to be opposed to each other.

According to a sixth aspect of the present invention, in the X-ray therapy system according to the first aspect, the irradiation unit includes: a kilo-voltage (kV)-X-ray irradiation unit configured to radiate kV-X-rays for acquiring at least either of an X-ray fluoroscopic image and an X-ray CT image; and a mega-voltage (MV) beam irradiation unit configured to radiate MV beams for treating a lesion portion within a body of the patient. Then, the pair of photon detection units are arranged on a line intersecting both an irradiation direction of the kV-X-rays and an irradiation direction of the MV beams.

An irradiation field determining method according to a seventh aspect of the present invention is an irradiation field determining method using the X-ray therapy system according to any one of the first to sixth aspects, the irradiation field determining method includes: acquiring an image of the patient using the pair of photon detection units from a predetermined direction in which the X-rays are radiated and identifying that a lesion portion is included within an irradiation field of MV beams based on the image; rotating, by the rotation-driving unit, the irradiation unit provided in the gantry by rotating the gantry and setting an irradiation direction of the X-rays from the irradiation unit as the predetermined direction; and radiating the X-rays from the irradiation unit in the predetermined direction.

According to the irradiation field determining method according to the above-described aspect, for example, axes of the one pair of photon detection units are set to be consistent with an MV beam irradiation direction immediately before the therapy, and a two-dimensional position of the X-ray irradiation target is determined by acquiring the image of the patient from a direction in which therapy MV beams are radiated. Next, the MV beam irradiation direction is caused to be consistent with the axes of the photon detection units by rotating the gantry. As a result, it is possible to accurately radiate the X-rays to the determined position.

According to an eighth aspect of the present invention, in the irradiation field determining method according to the seventh aspect, the irradiation field determining method further includes: rotating the pair of photon detection units provided in the gantry by which the rotation-driving unit rotates the gantry after the acquisition of the image and before the irradiation of the X-rays; setting a direction different from the predetermined direction as a second predetermined direction and acquiring a second image of the patient different from the image from the second predetermined direction using the pair of photon detection units; and determining a position of an irradiation target of the X-rays using at least the image and the second image from a start time of image acquisition using the photon detection units until X-ray irradiation using the irradiation unit starts.

In the irradiation field determining method according to the above-described aspect, the PET detection device having the pair of photon detection units may be adopted. The resolution within a photon detection surface may be high and the resolution of a direction perpendicular to the photon detection surface may be slightly low. On the other hand, it is possible to increase the resolution of the direction perpendicular to the photon detection surface by determining the position of the X-ray irradiation target using a plurality of images acquired by rotating the gantry. In addition, in this case, it is possible to accurately determine a three-dimensional position of the X-ray irradiation target.

According to a ninth aspect of the present invention, in the irradiation field determining method according to the seventh or eighth aspect, the position of the irradiation target is determined by superimposing an X-ray fluoroscopic image and a PET image.

According to a tenth aspect of the present invention, in the irradiation field determining method according to the seventh or eighth aspect, the irradiation field determining method further includes: generating a therapy plan for the patient based on an image obtained using the pair of photon detection units; and radiating the X-rays from the irradiation unit to the patient according to the therapy plan. Because of this, for example, when the therapy plan for the patient is generated, it is also possible to evaluate the irradiation unit based on the image obtained using the pair of photon detection units.

According to an eleventh aspect of the present invention, in the irradiation field determining method according to the eighth aspect, the irradiation field determining method further includes identifying that the lesion portion is included within an irradiation field of the MV beams based on the image and the second image.

Advantageous Effects of Invention

According to the above-described radiation therapy system, it is possible to accurately reflect a result of detecting a position of a lesion portion according to PET examination in an irradiation position of radiation from the irradiation unit. Further, because the photon detection unit-moving devices retract the pair of photon detection units when the radiation is radiated from the irradiation unit, it is possible to suppress an influence of the radiation radiated from the irradiation unit on the photon detection units.

DESCRIPTION OF EMBODIMENTS

Figure 1:
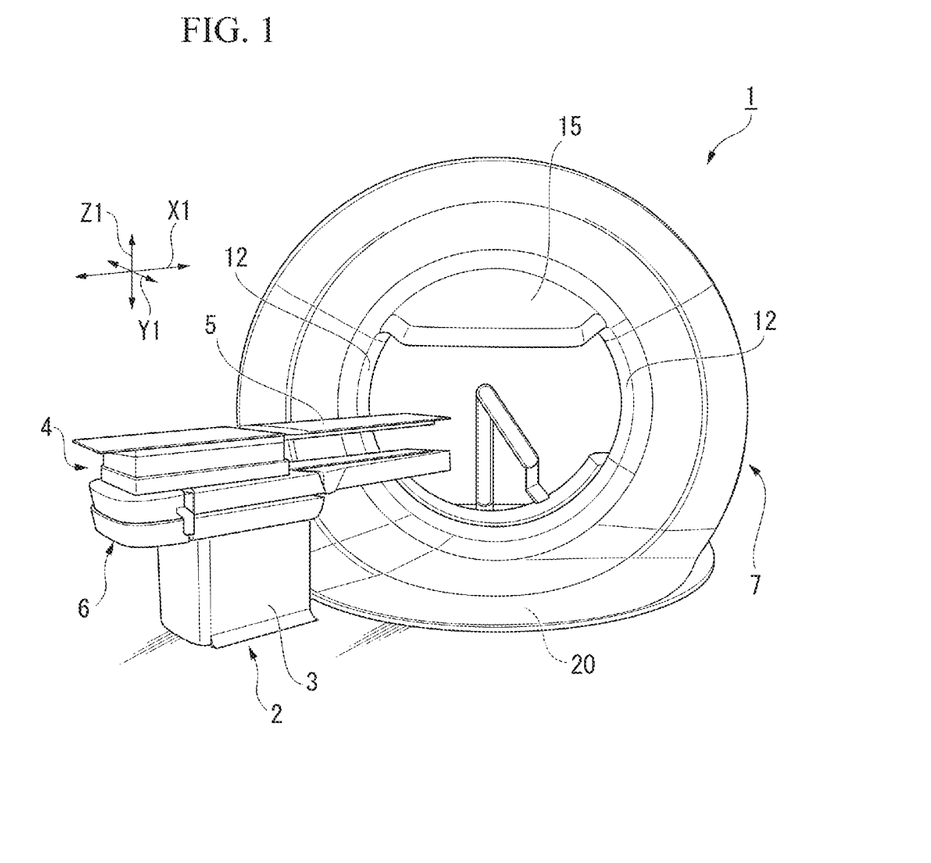
FIG. 1 is a front view illustrating a radiation therapy system according to an embodiment of the present invention.

A radiation therapy system (for example, an X-ray therapy system) according to an embodiment of the present invention will be described. FIG. 1 is a front view illustrating the radiation therapy system 1 according to this embodiment.

The radiation therapy system according to this embodiment is a system having a device for performing therapy by radiating radiation into a body of a patient.

As illustrating in FIG. 1, the radiation therapy system 1 includes a couch 2, an O-ring unit 7 having a ring-shaped gantry 11, a PET detection device 12, an irradiation unit 15, and a rotation-driving unit 20.

The couch 2 is a device on which the patient lies within the gantry 11. The couch 2 has a base portion 3, a bed 4 configured to relatively move with respect to the base portion 3, and a moving mechanism 6 configured to relatively move the bed 4 with respect to the base portion 3.

The base portion 3 is placed on or fixed to a floor surface on which the radiation therapy system 1 is installed, and has a height corresponding to a dimension of a height direction of the gantry 11. The height of the base portion 3 is configured as a height of a degree to which the bed 4 can be arranged at approximately the center of the ring-shaped gantry 11, and the accurate position of the bed 4 is defined by the moving mechanism 6.

The bed 4 has an approximately flat top surface portion 5. The top surface portion 5 is configured so that the patient lies in a sleeping state or another body position necessary for diagnosis or therapy.

The moving mechanism 6 has a vertical axis Z1 and two horizontal axes X1 and Y1 perpendicular to each other as degrees of freedom. That is, the moving mechanism 6 is capable of moving the bed 4 back and forth in the direction of the vertical axis Z1, rotating and moving the bed 4 around the vertical axis Z1, moving the bed 4 back and forth in directions of the horizontal axes X1 and Y1, and rotating and moving the bed 4 around the horizontal axes X1 and Y1. The moving mechanism 6 is configured to move the bed 4 based on a result of detection by the PET detection device 12 to be described later.

Figure 2:
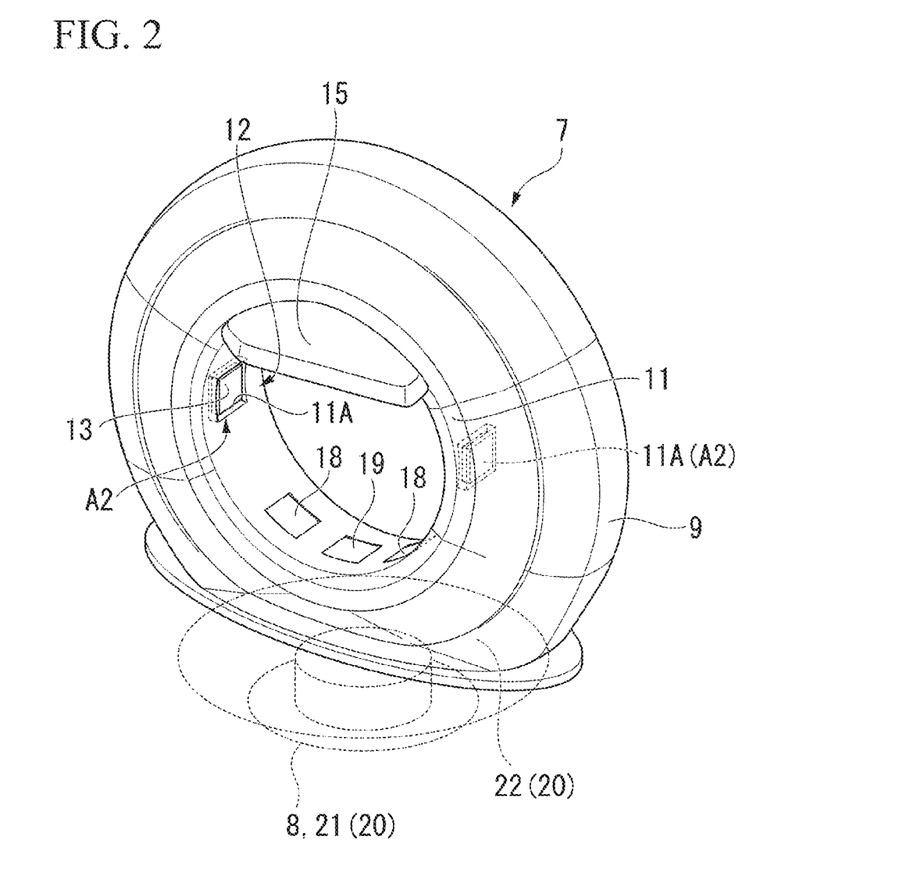
FIG. 2 is a perspective view illustrating part of the radiation therapy system according to the embodiment of the present invention.
Figure 3:
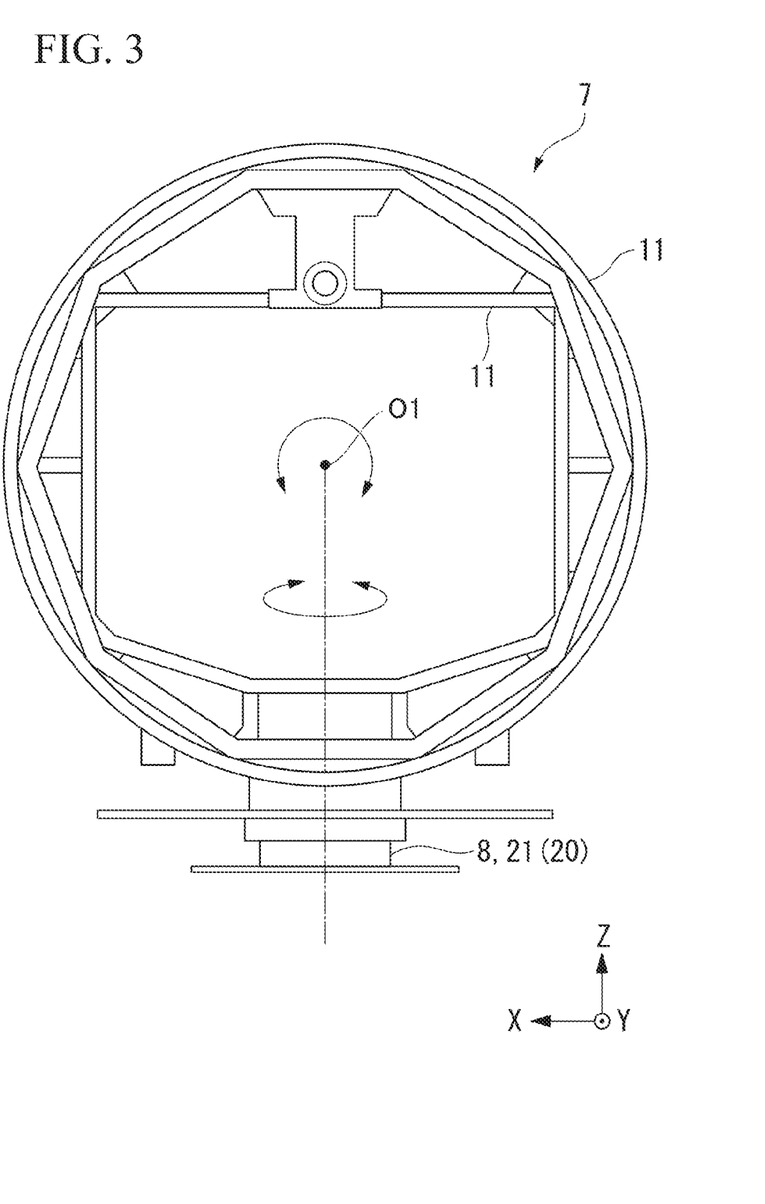
FIG. 3 is a front view illustrating an internal structure of the radiation therapy system according to the embodiment of the present invention.
Figure 4:
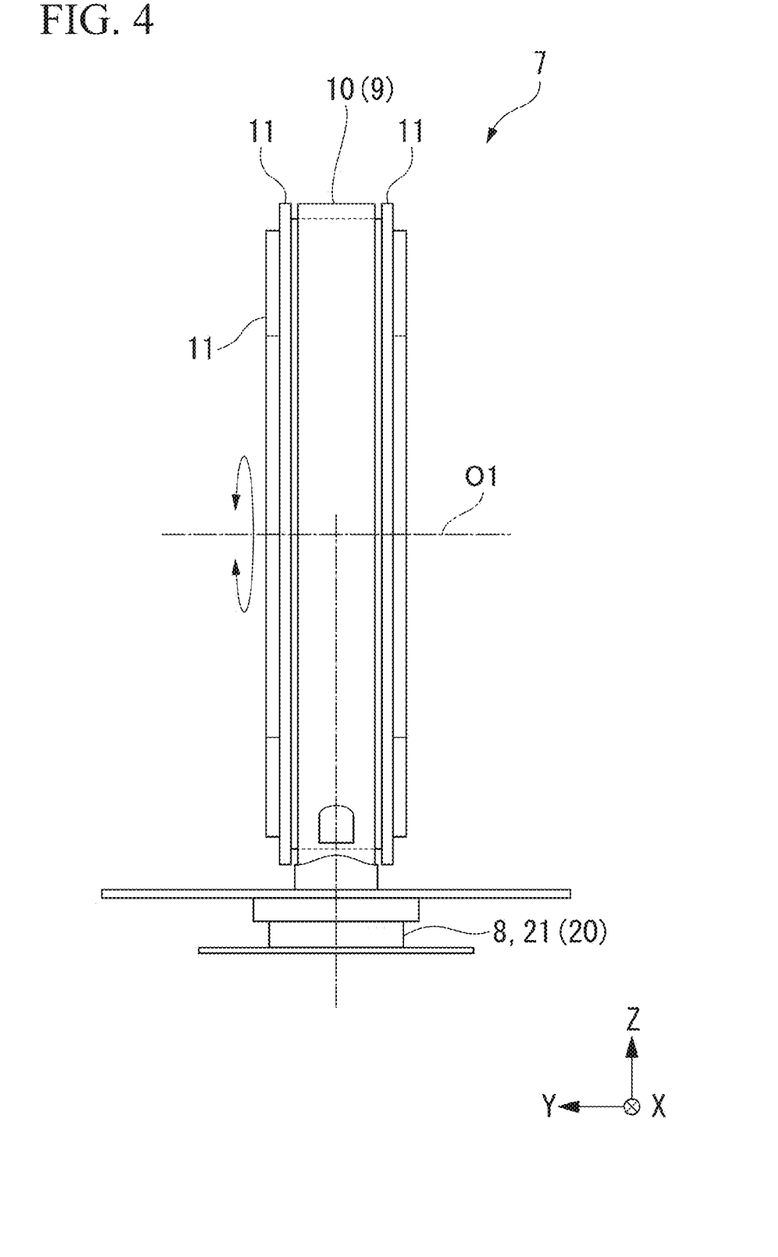
FIG. 4 is a perspective view illustrating the internal structure of the radiation therapy system according to the embodiment of the present invention.

FIG. 2 is a perspective view illustrating part of the radiation therapy system 1 according to this embodiment. FIG. 3 is a front view illustrating an internal structure of the radiation therapy system 1 according to this embodiment. FIG. 4 is a perspective view illustrating the internal structure of the radiation therapy system 1 according to this embodiment.

The O-ring unit 7 illustrated in FIG. 2 is a mechanism for enabling the patient lying on the bed 4 of the couch 2 illustrated on FIG. 1 to be arranged, diagnosed, and treated inside the O-ring unit 7. As illustrated in FIGS. 2 to 4, the O-ring unit 7 includes a base 8, a ring-shaped main body unit 9, and a gantry 11 connected to the main body unit 9.

The base 8 is fixed to the floor surface on which the radiation therapy system 1 is installed, and supports the entire main body unit 9. In this embodiment, part of the base 8 is placed within the floor surface, and a horizontal swing unit 21 which is part of the rotation-driving unit 20 in this embodiment is placed on the base 8. The horizontal swing unit 21 is a device for rotating and driving the O-ring unit 7 in a predetermined angle range around a vertical axis passing through a rotation center O1 of the gantry 11.

The main body unit 9 has a ring-shaped frame 10 having a lower end portion connected to the base 8. The main body unit 9 is swung by the horizontal swing unit 21 provided in the base 8 around the vertical axis. In this embodiment, the center of the ring-shaped frame 10 in the main body unit 9 is consistent with the rotation center O1 of the gantry 11 and serves as an isocenter in the radiation radiated from the irradiation unit 15.

The gantry 11 is a ring-shaped member which is placed inside the frame 10 of the main body unit 9 and rotates and moves along the frame 10. The PET detection device 12, the irradiation unit 15 from which the radiation is radiated, and the circumferential direction rotation unit 22 of the rotation-driving unit 20 are attached to the gantry 11.

Figure 5:
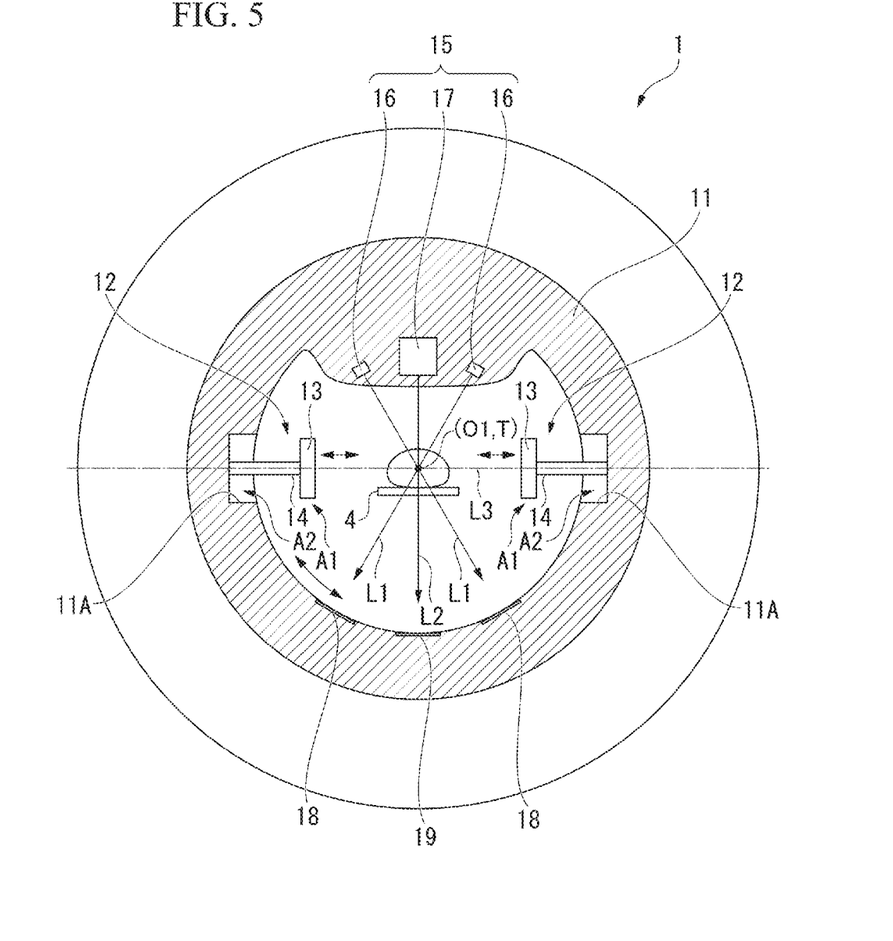
FIG. 5 is a partial cross-sectional view illustrating a PET detection device in the radiation therapy system according to the embodiment of the present invention.

FIG. 5 is a partial cross-sectional view illustrating the PET detection device 12 in the radiation therapy system 1 according to this embodiment.

As illustrated in FIG. 5, the PET detection device 12 is provided to perform positron emission tomography (PET) on the patient and has a pair of photon detection units 13 and photon detection unit-moving devices 14.

The pair of photon detection units 13 are provided to be opposed to each other with the patient interposed therebetween for the purpose of detecting photons emitted from the patient based on nuclear decay of a tracer nuclide administered to the patient. That is, the pair of photon detection units 13 are arranged to be opposed to each other with a predetermined rotation center O1 interposed therebetween in the gantry 11. In addition, in this embodiment, the radiation is radiated from the irradiation unit 15 to the rotation center O1 of the gantry 11, and the predetermined rotation center O1 serves as the isocenter in the radiation therapy system 1.

In this embodiment, each of the pair of photon detection units 13 has a flat plate shape. In addition, the photon detection units 13 are connected to a PET diagnosis computer system (not illustrated).

The photon detection unit-moving device 14 is a device configured to connect the photon detection units 13 to the gantry 11 and move the photon detection units 13 with respect to the gantry 11. In this embodiment, the photon detection unit-moving devices 14 are provided for the purpose of suppressing a negative influence on the photon detection units 13 as the radiation radiated from the irradiation unit 15 or the scattered rays of the radiation hit the photon detection units 13. That is, when the photons are detected in the PET examination, the photon detection unit-moving devices 14 arrange the pair of photon detection units 13 at positions (examination positions A1) separated from the patient by a predetermined distance. In addition, when the radiation is radiated from the irradiation unit 15 to the patient, the photon detection unit-moving devices 14 move the pair of photon detection units 13 from the patient to retraction positions A2 which are positions separated from the patient by a distance which is greater than the above-described predetermined distance before the irradiation of the radiation starts as necessary.

For the retraction positions A2, positions are set based on an irradiation direction and an irradiation range of the radiation radiated from the irradiation unit 15. The retraction positions A2 are located outside the irradiation range of the radiation and outside a range in which the scattered rays due to the radiation are capable of reaching the photon detection units 13. Specifically, the retraction positions A2 are provided within the gantry 11. In this embodiment, openings for a pair of concave portions 11A into which the pair of photon detection units 13 are inserted are formed in an inner circumferential surface of the gantry 11. Then, the insides of the concave portions 11A are set at the retraction positions A2 of the photon detection units 13. Further, the above-described photon detection unit-moving devices 14 are fixed to inner surfaces of the concave portions 11A. In addition, it is possible to place cover members configured to shield the radiation or scattered rays in the opening portions of the concave portions 11A as necessary.

In addition, the photon detection unit-moving devices 14 can change a distance between the photon detection units 13 for the patient. For example, it is possible to adjust a balance between sensitivity and resolution in the PET examination by changing a distance between the pair of photon detection units 13 using the photon detection unit-moving device 14. In this embodiment, the above-described predetermined distance may be located within the irradiation range of the radiation or within a range in which the scattered rays due to the radiation are capable of reaching the photon detection units 13. This is because a negative influence on the photon detection unit 13 does not occur because no radiation is radiated from the irradiation unit 15 when the PET examination is performed.

It is possible to appropriately select and adopt a known structure such as a linear motion mechanism using a ball screw, an expansion mechanism using a pantograph, or the like as a structure of the photon detection unit-moving device 14.

The irradiation unit 15 illustrated in FIG. 5 radiates the radiation emitted by a radiation generation source (not illustrated) to the patient. The irradiation unit 15 has kV-X-ray irradiation units 16 and a MV beam irradiation unit 17. The kV-X-ray irradiation units 16 radiate the kV-X-ray radiation for performing X-ray fluoroscopic photographing and acquiring an X-ray CT image. The MV beam irradiation unit 17 radiates MV beams for treating the lesion portion T within a body of the patient.

In this embodiment, the kV-X-ray irradiation units 16 are provided at two positions with the MV beam irradiation unit 17 interposed therebetween. In addition, kV-X-ray detection units 18 are provided on sides opposed to the kV-X-ray irradiation units 16 with the rotation center O1 interposed therebetween. In addition, an MV beam detection unit 19 is provided on a side opposed to the MV irradiation unit 17 with the rotation center O1 interposed therebetween.

Here, a positional relationship among the irradiation unit 15 and the photon detection units 13 will be described.

As illustrated in FIG. 5, the pair of photon detection units 13 are arranged on a line intersecting both an irradiation direction L1 of the kV-X-rays and an irradiation direction L2 of the MV beams. Specifically, the photon detection units 13 are arranged on a line L3 orthogonal to a straight line connecting the MV beam irradiation unit 17 and the MV beam detection unit 19 and the pair of photon detection units 13 are configured to operate back and forth along the line L3. In this embodiment, the straight line connecting the MV beam irradiation unit 17 and the MV beam detection unit 19 is consistent with a line representing the above-described irradiation direction L2.

The rotation-driving unit 20 causes the gantry 11 to perform a rotational movement around a predetermined rotation center O1. In this embodiment, the "predetermined rotation center O1" is a center point of the gantry 11 formed in a ring shape. In addition, the rotation-driving unit 20 includes a horizontal swing unit 21 and a circumferential direction rotation unit 22. The horizontal swing unit 21 is provided to cause the gantry 11 to rotate around a vertical axis passing through the center point. The circumferential direction rotation unit 22 is provided to cause the gantry 11 to rotate in a circumferential direction with respect to the frame 10. The horizontal swing unit 21 and the circumferential direction rotation unit 22 can operate independently of each other.

The rotation-driving unit 20 causes the irradiation unit 15 and the PET detection device 12 to perform the rotational movement around the predetermined rotation center O1 by causing the gantry 11 to perform the rotational movement around the predetermined rotation center O1. Thereby, the irradiation unit 15 and the PET detection device 12 are integrally moved in a state in which a relative positional relationship among the irradiation unit 15 and the PET detection device 12 is maintained.

Figure 6:
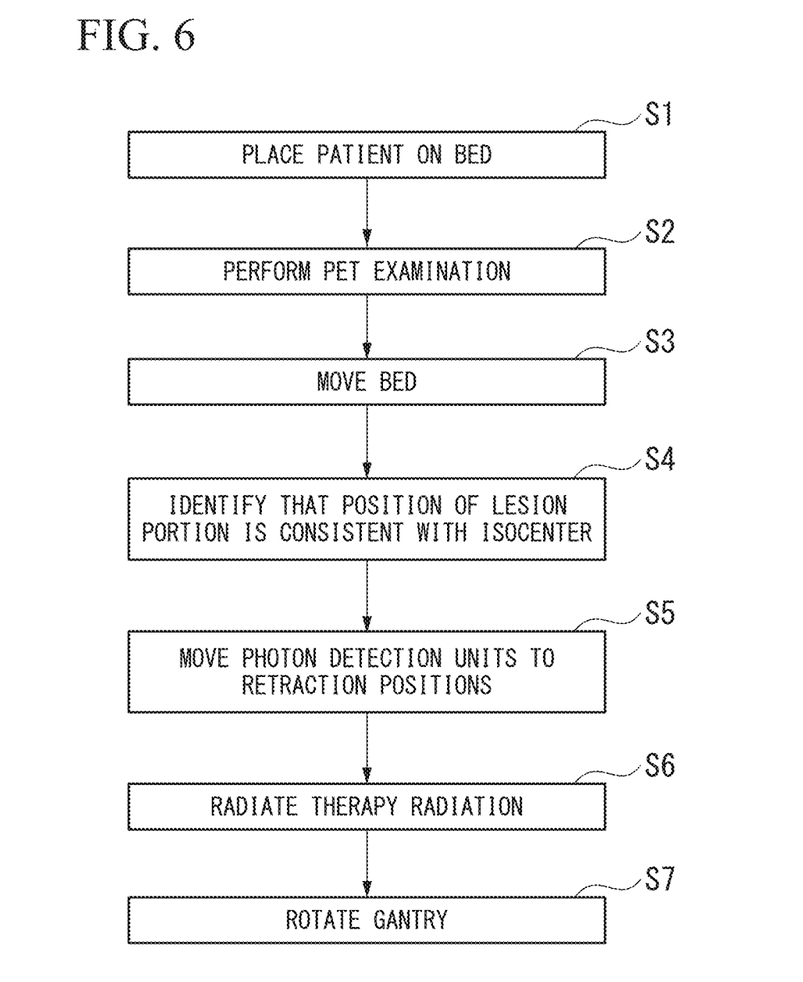
FIG. 6 is a flowchart illustrating an operation when the radiation therapy system according to the embodiment of the present invention is used.

Next, an operation of the radiation therapy system 1 according to this embodiment and an irradiation field determining method using the radiation therapy system 1 will be described along with the therapy method using the radiation therapy system 1. FIG. 6 is a flowchart illustrating an operation when the radiation therapy system 1 according to this embodiment is used.

When the radiation therapy system 1 is used, a tracer nuclide specific to the lesion portion T is first administered. Thereafter, the patient lies on the bed 4 of the couch 2. Further, it is identified that the patient is held at a body position at which radiation suitable for a position of the lesion portion T found by pre-examination can be radiated (step S1 illustrated in FIG. 6). A type of tracer nuclide can be appropriately selected in correspondence with an examination target.

Next, as in the conventional therapy, setup is performed with high accuracy by matching with an image at the time of a therapy plan of the patient using X-ray photographing or cone-beam CT.

Subsequently, the PET examination is performed using the PET detection device 12 and the PET diagnosis computer system (step S2).

In the PET examination, the photon detection units 13 first move to a position at which a detection process can be performed in a direction in which therapy beams are radiated, and the lesion portion T is positioned between the pair of photon detection units 13. Then, at the timing at which a tracer nuclide administered to the patient decays, photons are emitted out of the body of the patient. When the photons reach the pair of photon detection units 13 arranged to be opposed to each other with the patient interposed therebetween, detection signals are output from the photon detection units 13 to the PET diagnosis computer system. In the PET diagnosis computer system, a position at which the tracer nuclide has decayed is specified within a three-dimensional space based on a state in which the photons are incident on the photon detection unit 13. In the PET examination, a portion in which the concentration of the tracer nuclide is high is detected based on information of the position at which the tracer nuclide has decayed, and three-dimensional position information is obtained. Because the tracer nuclide is specifically accumulated into the lesion portion T, the three-dimensional position information of the lesion portion T is obtained by the PET examination. In this embodiment, it is possible to acquire the three-dimensional position information of the lesion portion T with high resolution by performing the PET examination in two directions of the front and the side because the resolution of a photon detector surface direction is excellent.

Next, based on the three-dimensional position information of the lesion portion T obtained in the PET examination, the bed 4 is moved by the moving mechanism 6 so that the position of the lesion portion T is consistent with the isocenter (the predetermined rotation center O1 in this embodiment) (step S3). Thereafter, it is identified that the position of the lesion portion T is consistent with the isocenter by the PET examination if necessary (step S4).

Figure 7:
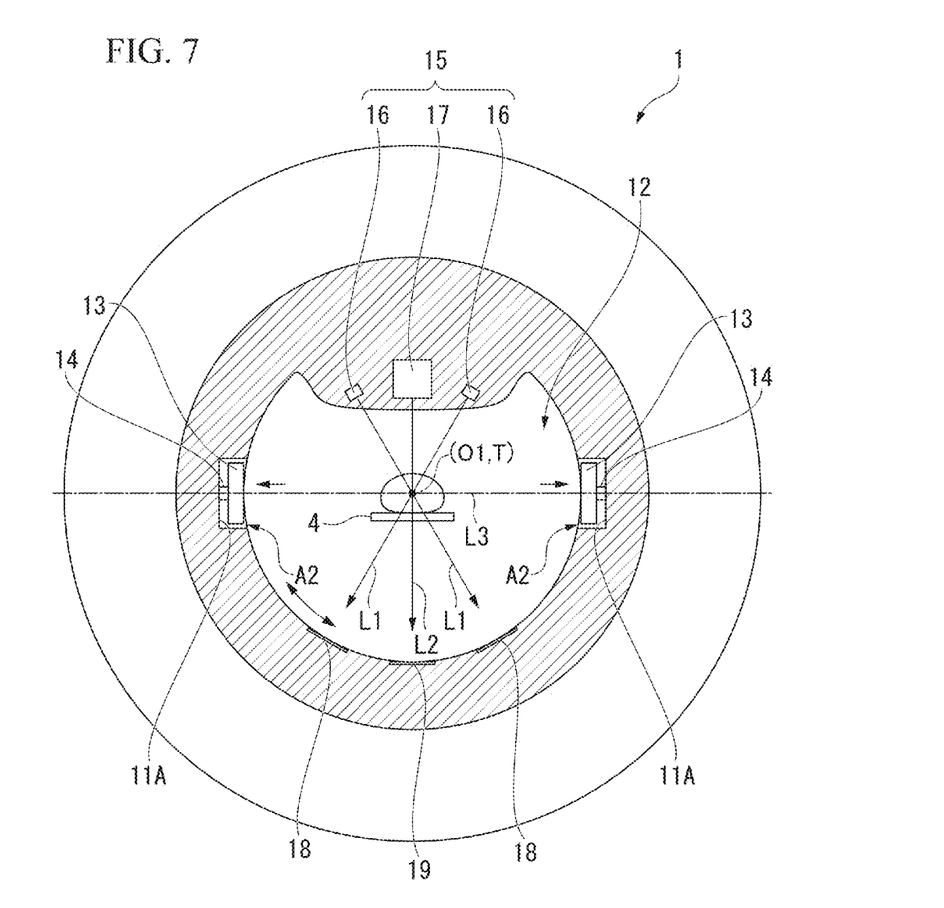
FIG. 7 is an explanatory diagram illustrating a process when the radiation therapy system according to the embodiment of the present invention is used.

FIG. 7 is an explanatory diagram illustrating a process when the radiation therapy system 1 according to this embodiment is used. A state in which the photon detection units 13 are moved to the retraction positions A2 is shown after the end of the PET examination as necessary.

After it is identified that the position of the lesion portion T is consistent with the isocenter by the PET examination, the photon detection units 13 are moved into the concave portions 11A by the photon detection unit-moving device 14

(step S5, see FIG. 7). Thereby, the photon detection units 13 are arranged at the retraction positions A2 at which there is no influence of the radiation radiated from the irradiation unit 15.

Subsequently, the irradiation unit 15 is moved to an irradiation position by the rotation of the gantry 11 and then the MV beams are radiated to the isocenter (step S6). The patient lying on the bed 4 maintains a posture at the end of the PET examination because the couch 2 and the gantry 11 do not move during a period from the end of the PET examination to the beginning of MV beam irradiation. Thereby, at the time of the MV beam irradiation, the position of the lesion portion T of the patient is located at the isocenter.

After MV beams of a necessary radiation dose are radiated to the lesion portion T, the irradiation of the MV beams from the irradiation unit 15 stops and the gantry 11 is moved by a predetermined angle in the circumferential direction of the frame 10 (step S7). For example, the gantry 11 stops after moving 45 degrees in the circumferential direction of the frame 10. Thereby, the angle of the PET detection device 12 for the lesion portion T and the angle of the irradiation unit 15 for the lesion portion T are shifted by the above-described predetermined angle. In a new positional relationship in which the PET detection device 12 and the irradiation unit 15 are shifted by the predetermined angle, the steps from the above-described step S2 to the above-described step S6 are performed in order and the MV beams are radiated to the lesion portion T. Thereafter, the gantry 11 is rotated in the circumferential direction of the frame 10 by performing the above-described step S7 again.

Also, the step (the above-described step S4) of identifying the position by the PET examination can also be omitted if unnecessary.

By iterating steps S2 to S7, it is possible to radiate MV beams from a different angle with respect to the isocenter. At this time, it is possible to start the irradiation of the radiation without moving the bed 4 after the PET examination is performed. Thereby, it is possible to reduce the possibility of the posture of the patient on the bed 4 being changed or the position of the patient being shifted by moving the bed 4.

In addition, as another usage method of the radiation therapy system 1 according to this embodiment, the gantry 11 is rotated before the MV beams are radiated from the irradiation unit 15 and a plurality of PET examination images may be acquired from angles at which the MV beams are radiated. Thereafter, it is possible to rotate the gantry 11 and set the MV beam irradiation unit at the above-described angles to radiate the MV beams.

As described above, according to the radiation therapy system 1 of this embodiment, a result of detecting the position of the lesion portion T by the PET examination is accurately reflected in the irradiation position of the radiation from the irradiation unit 15. Thereby, it is possible to find an accurate position of the lesion portion T immediately before the therapy beams (for example, MV beams) are radiated. As a result, accurate therapy can be performed by identifying an affected area using a beam's eye view (BEV).

In addition, it is possible to acquire images of the lesion portion T in a plurality of directions using the PET detection device 12 provided in the rotating gantry 11 as means for increasing the resolution of a direction perpendicular to the photon detection surface for the resolution within the photon detection surface and identify a three-dimensionally accurate position of the lesion portion T. For example, it is possible to image an accurate position of the lesion portion T by acquiring one PET examination image at every 45 degrees around the rotation center of the gantry 11 and superimposing a plurality of PET examination images. In addition, it is also possible to identify a three-dimensional tumor position from this result.

Further, according to the radiation therapy system 1 of this embodiment, it is possible to suppress an influence on the photon detection units 13 due to the radiation radiated from the irradiation unit 15 because the photon detection unit-moving devices 14 retract the pair of photon detection units 13 when the radiation is radiated from the irradiation unit 15.

In addition, because the gantry 11 has a ring shape according to the radiation therapy system 1 of this embodiment, it is possible to perform therapy with high rigidity and high positional accuracy as compared to when the conventional C-arm structure is provided. Further, because the pair of photon detection units 13 are arranged on the ring-shaped gantry 11 with high rigidity, the irradiation unit 15 and the photon detection units 13 do not interfere with each other while maintaining high positional accuracy.

In addition, by inserting and arranging the photon detection units 13 inside the concave portions 11A provided in the gantry 11 according to the radiation therapy system 1 of this embodiment, it is possible to shield part of the radiation and its scattered rays through the gantry 11.

In addition, according to the radiation therapy system 1 of this embodiment, the pair of photon detection units 13 are arranged to be opposed to each other with the isocenter interposed therebetween. As a result, it is possible to preferably perform PET examination in a state in which the pair of photon detection units 13 are placed at positions which do not interfere with the kV-X-ray irradiation unit 16, the MV beam irradiation unit 17, the kV-X-ray detection unit 18, and the MV beam detection unit 19 in the irradiation unit 15.

In addition, in the PET examination using the photon detection units 13 arranged to be opposed to each other, a change in the resolution due to a distance between the pair of photon detection units 13 is small. Because of this, it is possible to perform high-sensitivity PET examination by placing the pair of photon detection units 13 in the vicinity of the patient during the PET examination.

Further, according to the radiation therapy system 1 of this embodiment, it is possible to perform X-ray fluoroscopic photographing and both CT examination and PET examination. Because of this, for example, it is possible to reliably specify the position of the lesion portion T by solving a mutual problem through the identification of the lesion portion T by the PET examination or the like when it is difficult to identify the lesion portion T in an X-ray fluoroscopic image.

Although the embodiments of the present invention have been described above in detail with reference to the drawings, specific configurations are not limited to the embodiments, and a design change and the like may be included without departing from the scope of the present invention.

For example, in the above-described embodiment, a description of the case in which X-ray fluoroscopic photographing and CT examination using kV-X rays are performed is omitted. However, the X-ray fluoroscopic photographing and the CT examination may be performed at the timing immediately before and/or after the PET examination as necessary. In addition, setup by an X-ray fluoroscopic image or an X-ray CT image can also be performed between step 1 (S1) and step 2 (S2).

In addition, it is possible to obtain detailed position information and shape information of the lesion portion T by superimposition of images obtained by the PET examination by moving the gantry 11 in the circumferential direction of the frame 10 and performing the PET examination at every predetermined angle without radiating the radiation. The radiation may be radiated by performing steps from the above-described step S2 to the above-described step S7 using the detailed position information and shape information obtained as described above.

In addition, according to the radiation therapy system 1 of this embodiment, it is possible to create a therapy plan using an image obtained by the PET examination and radiate the radiation according to the therapy plan immediately after diagnosis by the PET examination. For example, it is possible to obtain a high therapy effect because therapy can be quickly performed by omitting pre-examination using another device for creating a therapy plan in the case of bone metastasis.

In addition, an example in which the therapy of the patient is performed by radiating therapy X-rays to the patient has been shown in the above-described embodiment. However, it is possible to similarly configure a device for performing the therapy of the patient and an irradiation field determining method by radiating radiation other than the X-rays or particle rays instead of the radiation.

EXAMPLE

Next, the radiation therapy system of the present invention will be described in further detail using an example.

In this example, sensitivity and accuracy were considered when the position of the lesion portion was identified by comparing the radiation therapy system described in the above-described embodiment to an existing opposed PET device.

In the following Table 1, a configuration of the existing opposed PET device (comparative example) and a configuration of the PET detection device (example) in this example are shown.

TABLE 1

|  | COMPARATIVE EXAMPLE | EXAMPLE |
| --- | --- | --- |
| NUMBER OF DETECTION ELEMENTS | 1,980 × 2 = 3,960 | 11,664 × 2 = 23,328 |
| CRYSTAL SIZE | 2 × 2 × 20 mm$^3$ | 2.5 × 2.5 × 25 mm$^3$ |
| DETECTION AREA | 16 × 16 cm$^2$ | 40 × 40 cm$^2$ |

Figure 8A:
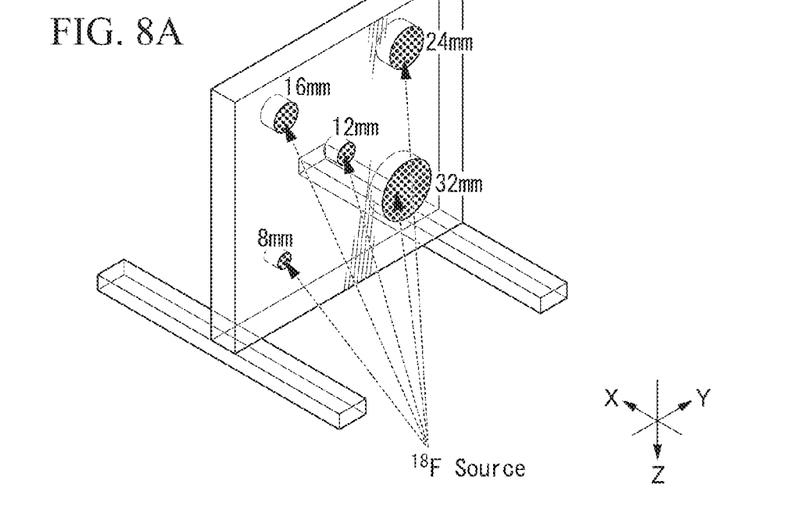
FIG. 8A is a schematic diagram illustrating an experimenting device for considering photon detection states in the PET detection device according to the embodiment and an existing opposed PET device.
Figure 8B:
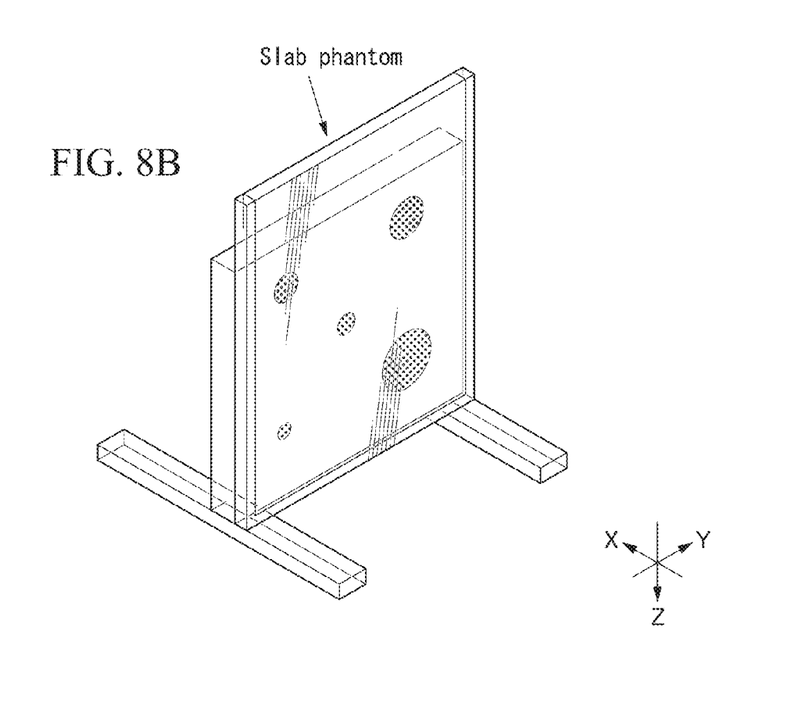
FIG. 8B is a schematic diagram illustrating an experimenting device for considering the photon detection states in the PET detection device according to the embodiment and the existing opposed PET device.
Figure 9:
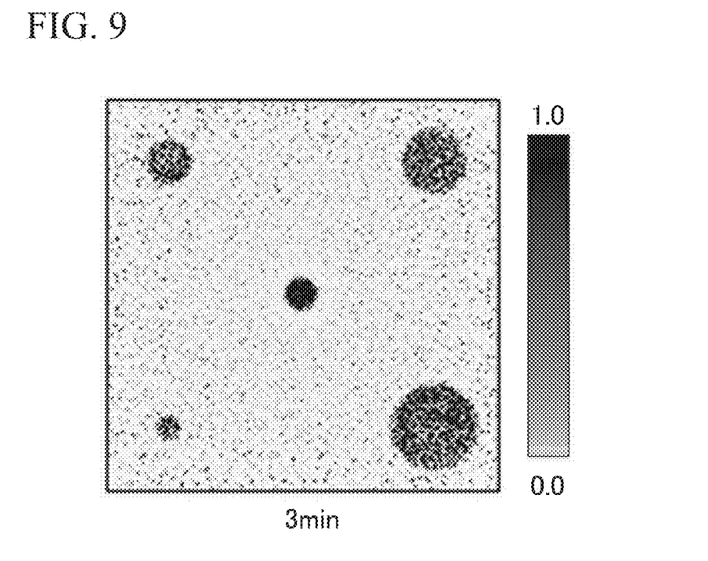
FIG. 9 is a diagram illustrating a detection result using the PET detection device according to the embodiment.
Figure 10:
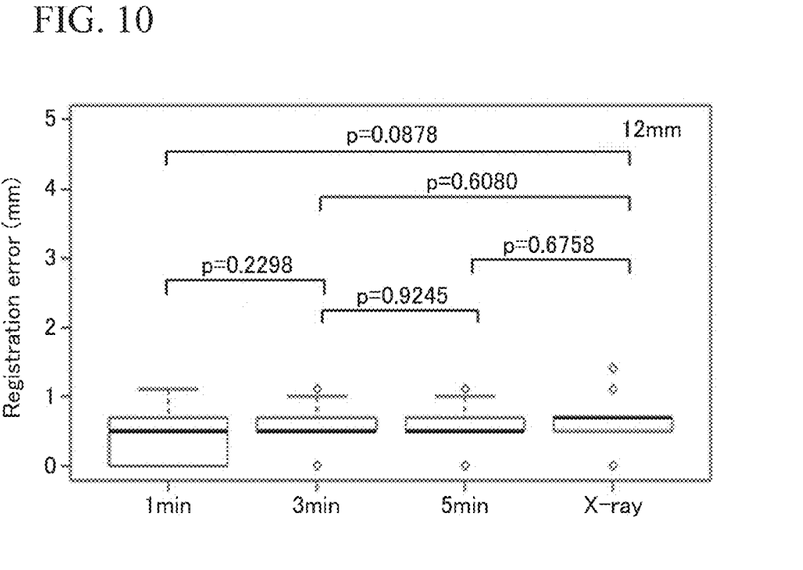
FIG. 10 is a graph illustrating a detection result using the PET detection device according to the embodiment and a detection result using the existing opposed PET device.

In addition, FIGS. 8A and 8B are schematic diagrams illustrating an experimenting device for considering photon detection states in the PET detection device according to this embodiment and an existing opposed PET device, respectively. FIG. 9 is a diagram illustrating a detection result (example) using the PET detection device according to this embodiment. FIG. 10 is a graph illustrating the accuracy of position alignment when the PET detection device according to this embodiment is used. In FIG. 10, three left bars represent position errors (registration errors) when exposure times for a radiation source (a radiation source having a diameter of 12 mm in FIG. 8A) designed in imitation of an 18F radioactive tracer nuclide are 1 min, 3 min, and 5 min, and the rightmost bar represents the registration error in a control experiment using an X-ray fluoroscopic device.

As illustrated in FIGS. 8A and 8B, in this example and the comparative example, a slab phantom was used and an existing X-ray fluoroscopic device and the PET detection device according to this embodiment were compared.

As illustrated in FIG. 9, the PET detection device according to this embodiment obtained an image of the radiation source as in the X-ray fluoroscopic device. In addition, as illustrated in FIG. 10, in the PET detection device according to this embodiment, an error of position alignment is 1 mm or less and the position of the lesion portion can be identified with accuracy which falls within a setup margin as suggested.

In addition, because the number of detection elements is large and a detection area is wide in this example as shown in the above-described Table 1, this example is considered to be advantageous in terms of sensitivity and resolution.

INDUSTRIAL APPLICABILITY

The above-described radiation therapy system can be applied to a device and a system for specifying a position at which radiation is radiated by PET examination and radiating the radiation to the specified position.

REFERENCE SIGNS LIST

1 Radiation therapy system
2 Couch
3 Base portion
4 Bed
5 Top surface portion
6 Moving mechanism
7 O-ring unit
8 Base
9 Main body unit
10 Frame
11 Gantry
11A Concave portion
12 PET detection device
13 Photon detection unit
14 Photon detection unit-moving device
15 Irradiation unit
16 kV-X-ray irradiation unit
17 MV beam irradiation unit
18 kV-X-ray detection unit
19 MV beam detection unit
20 Rotation-driving unit
21 Horizontal swing unit
22 Circumferential direction rotation unit
A1 Examination position
A2 Retraction position
L1 kV-X-ray irradiation direction
L2 MV beam irradiation direction
L3 Line representing layout and movement direction of photon detection units
O1 Rotation center
T Lesion portion
X1, Y1 Horizontal axis
Z1 Vertical axis

The invention claimed is:
1. An X-ray therapy system comprising:
a ring-shaped gantry in which a patient is to be arranged;
a positron emission tomography (PET) detection device in the gantry and configured to perform PET on the patient;
an irradiation unit in the gantry and configured to radiate X-rays to the patient; and
a rotation-driving unit for causing the gantry to perform a rotational movement around a predetermined rotation center,
wherein the gantry includes a concave portion on an inner circumferential surface thereof, wherein the concave portion includes a bottom surface at an outer peripheral side of the gantry and an opening at an inner peripheral side of the concave portion, wherein the gantry further includes a cover member for covering the opening of the concave portion, the cover member being configured to block the X-rays or scattered rays due to the X-rays from the irradiation unit, wherein the PET detection device includes:

photon detection units to detect photons emitted from the patient based on nuclear decay of a tracer nuclide administered to the patient; and a photon detection unit-moving device configured to move one of the photon detection units with respect to the gantry, wherein the photon detection units are on opposite sides from each other with the patient therebetween, wherein a first end of the photon detection unit-moving device is fixed to the one of the photon detection units, and a second end of the photon detection unit-moving device is fixed to the bottom surface of the concave portion, wherein the rotation-driving unit causes the irradiation unit and the PET detection device to perform the rotational movement around the predetermined rotation center by causing the gantry to perform the rotational movement around the predetermined rotation center, wherein, when detecting photons in the PET, the photon detection unit-moving device is configured to arrange the one of the photon detection units at a position separated from the patient by a predetermined distance, and wherein, when the X-rays are radiated from the irradiation unit to the patient, the one of the photon detection units moves away from the patient and is housed in a retraction position inside the concave portion before radiation of the X-rays starts.

2. The X-ray therapy system according to claim 1, wherein the retraction position is located outside a radiation range of the X-rays and outside a range in which scattered rays due to the X-rays are capable of reaching the one of the photon detection units, and wherein the predetermined distance is within the radiation range of the X-rays or within the range in which the scattered rays due to the X-rays are capable of reaching the one of the photon detection units.

3. The X-ray therapy system according to claim 1, wherein the photon detection units are arranged to interpose the predetermined rotation center.

4. The X-ray therapy system according to claim 1, wherein the photon detection units are arranged to interpose an isocenter.

5. The X-ray therapy system according to claim 1, wherein the irradiation unit includes:

a kilo-voltage (kV)-X-ray irradiation unit configured to radiate kV-X-rays for acquiring at least either of an X-ray fluoroscopic image and an X-ray CT image; and a mega-voltage (MV) beam irradiation unit configured to radiate MV beams for treating a lesion portion within a body of the patient, and wherein the photon detection units are arranged on a line intersecting both an irradiation direction of the kV-X-rays and an irradiation direction of the MV beams.

6. An irradiation field determining method using the X-ray therapy system according to claim 1, the irradiation field determining method comprising:

acquiring an image of the patient using the photon detection units from a predetermined direction in which the X-rays are radiated and identifying that a lesion portion is included within an irradiation field of MV beams based on the image;

rotating, by the rotation-driving unit, the irradiation unit in the gantry by rotating the gantry and setting an irradiation direction of the X-rays from the irradiation unit as the predetermined direction; and radiating the X-rays from the irradiation unit in the predetermined direction.

7. The irradiation field determining method according to claim 6, wherein the image is a first image, the predetermined direction is a first predetermined direction and the irradiation field determining method further comprises:

rotating the photon detection units in the gantry by which the rotation-driving unit rotates the gantry after the acquisition of the image and before the radiation of the X-rays;

setting a direction different from the first predetermined direction as a second predetermined direction and acquiring a second image of the patient from the second predetermined direction using the photon detection units, the second image being different from the first image; and determining a position of a radiation target of the X-rays using at least the first image and the second image from a start time of image acquisition using the photon detection units until X-ray radiation using the irradiation unit starts.

8. The irradiation field determining method according to claim 6, wherein the position of the radiation target is determined by superimposing an X-ray fluoroscopic image and a PET image.

9. The irradiation field determining method according to claim 6, further comprising:

generating a therapy plan for the patient based on the image obtained using the photon detection units, radiating the X-rays from the irradiation unit to the patient according to the therapy plan.

10. The irradiation field determining method according to claim 7, further comprising:

identifying that the lesion portion is included within the irradiation field of the MV beams based on the first image and the second image.

* * * * *